United States Patent [19]
Stark et al.

[11] 3,970,426
[45] July 20, 1976

[54] METHOD AND APPARATUS FOR THE PRESTERILIZATION OF PACKING MACHINES

[75] Inventors: Sven Olof Sören Stark, Rydsgard; Jan Axel Ingemar Rausér; Irma Marita Rausér, both of Lomma, all of Sweden

[73] Assignee: Deering Milliken Research Corporation, Spartanburg, S.C.

[22] Filed: Mar. 11, 1975

[21] Appl. No.: 557,398

[30] Foreign Application Priority Data
Mar. 18, 1974 Sweden .............................. 7435825

[52] U.S. Cl. ................................ 21/54 R; 21/74 A; 21/102 R; 21/DIG. 2
[51] Int. Cl.² ..................... A61L 3/00; A61L 13/06
[58] Field of Search ....... 21/2, 54 R, 102 R, DIG. 2, 21/74 A; 250/503, 504; 313/110, 112, 113; 426/399

[56] References Cited
UNITED STATES PATENTS

| | | |
|---|---|---|
| 2,810,652 | 10/1957 | Armbruster ........................ 53/28 X |
| 3,063,845 | 11/1962 | Graves ........................... 426/399 X |
| 3,269,079 | 8/1966 | Schmied ............................... 53/28 |
| 3,466,850 | 9/1969 | Hudson et al. ................ 21/102 R X |
| 3,674,421 | 7/1972 | Decupper ....................... 21/54 R X |

*Primary Examiner*—Morris O. Wolk
*Assistant Examiner*—Dale Lovercheck
*Attorney, Agent, or Firm*—Earle R. Marden

[57] ABSTRACT

Method and apparatus to pre-sterilize the filling tube of a packaging machine which produces filled flexible packages. The pre-sterilization is carried out by generating ozone within the confines of a tubular web of packaging material and recirculating the ozone through the filling tube while generating more ozone for sufficient time to pre-sterilize the machine.

5 Claims, 1 Drawing Figure

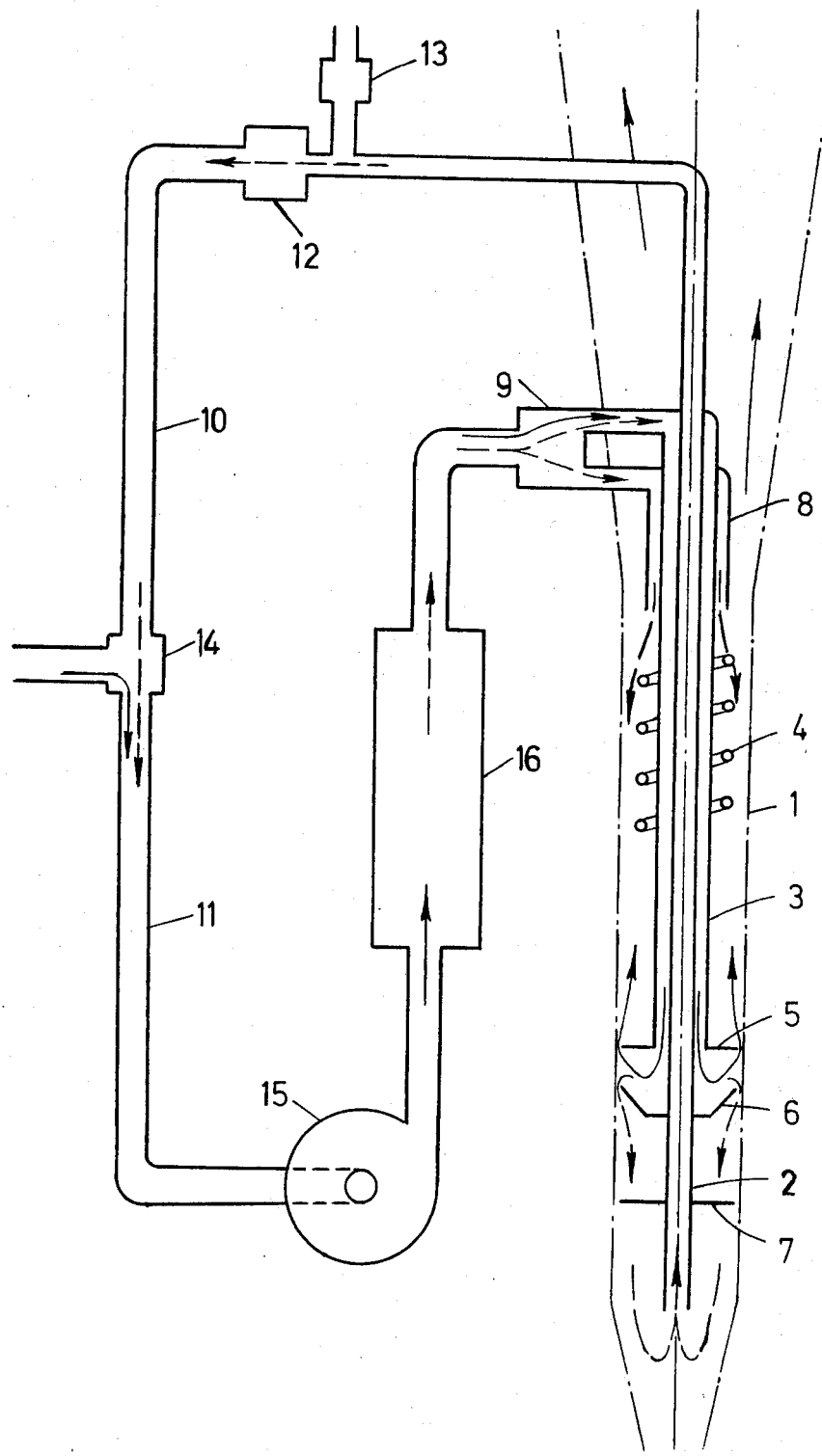

METHOD AND APPARATUS FOR THE PRESTERILIZATION OF PACKING MACHINES

The present invention relates to a method which, in machines for the continuous manufacture of packages sterilized by means of ultra-violet radiation, sterilizes the parts of the machine and the packing material which come into direct or indirect contact with the contents of the packages before the start-up of the machine and an arrangement for the realization of the method.

The method and the arrangement in accordance with the invention are specially intended to be used in the type of packing machines which manufacture continuously aseptic, separate packages, filled, e.g. with sterile milk, from a web of packing material passing through the packing machine. In this type of machine the conversion of the packing material web to separate, filled and sterile packages takes place usually by the shaping of the packing material web to a tube, sealing of the longitudinal joint of the tube, sterilization of the inside of the tube by ultra-violet radiation, filling of the tube and forming, sealing, and dividing of the tube into separate packages, a delivery tube for the contents extending inside the material tube and ending in the tube near the place at which the separate packages are formed. The sterilization of the inside of the tube thus takes place continuously when the material tube during operation passes the source of ultra-violet rays. At the same time the oxygen present in the air is converted to ozone, and since for various reasons it is not desirable that the contents, for example milk, should come into contact with the ozone, an air delivery opening is provided inside the tube between the source of ultra-violet rays and the place at which the contents are introduced into the tube, a continuous air stream being produced during operation from the air delivery opening and through the tube in the direction towards the growth end of the same, so that the ozone generated is entrained and is discharged through the open end of the tube.

At the start-up of a packing machine of the abovementioned type, after standstill, it is necessary to carry out a special pre-sterilization of those parts of the packing material and the machine which during operation come into contact with the milk. Namely pre-sterilization includes the inside of the delivery tubes for the contents and air, the outside of those parts of the delivery tubes which are located inside the packing material tube, the other parts of the machine which are located inside the packing material tube and at least that part of the inside of the packing material tube which is situated between the source of ultra-violet rays and the place at which the contents of the package are introduced. That is to say the part of the packing material which in the earlier operation has already passed the sterilizing source of ultra-violet rays.

The above-mentioned pre-sterilization of the machine and of the packing material has been carried out previously, mostly by introducing hot air or steam into the delivery tube for the contents of the packages via a valve, which is arranged on the delivery tube between the connection of the same to the source of the contents and the outlet located at the lower end of the tube. The hot air or steam thus follow the normal flowpath of the contents through the delivery tube and flow out into the material tube at the lower end of the same, whereupon the hot air flows upwards through the tube and is discharged at the growth end of the same. In the course of this a heating takes place for the bacteriological killing of the inside as well as of the outside of the delivery tube, the remaining parts of the machine located in the packing material tube and the inside of the tube material. This method of sterilization was complemented in certain cases in that a bactericide (e.g. hydrogen peroxide) in finely divided form was introduced into the hot air and followed the same through the delivery tube and the material tube.

The earlier pre-sterilization method comprised certain disadvantages. Thus it was necessary, for example, because of the high temperature of the hot air to provide cooling devices on the outside of the packing material tube so as to prevent the material from being overheated, which caused the material to become brittle and the moisture present in the paper to be transformed to steam, through which the durability and tightness of the longitudinal joint are appreciably reduced. In spite of the cooling device, however, a certain heating of the packing machine takes place which is not desirable. Even if the application of bactericides does not entail the above disadvantages, it is, of course, always desirable to reduce the employment of chemicals together with foodstuffs.

It is an object of the present invention to overcome the abovementioned disadvantages.

It is a further object of the present invention to provide a sterilization without heating or the use of chemicals.

It is a further object of the present invention to produce an arrangement for pre-sterilization which arrangement does not make the machine more complicated and expensive.

These and other objects were achieved in accordance with the invention, in that a method, which in a machine for the continuous manufacture of packages sterilized by means of ultra-violet radiation, sterilizes those parts of the machine and the packing material which come into direct or indirect contact with the contents of the packages before the start-up of the machine. The method is characterized in that the source of ultra-violet rays is activated, whereupon the oxygen converted to ozone by the ultra-violet radiation, preferably together with the air present is made to circulate through or come into contact with those parts which are to be sterilized, and in that an arrangement for the realization of the above-mentioned method is characterized in that a duct is arranged so as to make possible the circulation and recirculation of the ozone mixture, which duct comprises the parts of the machine and of the packing material which are to be sterilized.

The invention brings about a number of advantages. Through the method of utilizing the sterilizing effect of ozone it becomes possible effectively and without complicated units to carry out a sterilization of not readily accessible parts of the filling system of the packing machine. As a further result of the invention a number of pieces of equipment required previously becomes unnecessary, e.g. air superheaters and cooling devices. Through this, the machine can be made more compact and less complicated.

The invention will be described in detail in the following with reference to the enclosed drawing, which shows schematically a section through an arrangement in accordance with the invention together with filling unit and sterilizing arrangement in a packing machine of the known type.

The method and arrangement in accordance with the present invention will be described in connection with a packing machine of the type in which a web of packing material, for example plastic-coated paper, is introduced and, with continuous movement substantially vertically downwards through the machine, is formed to a tube 1, which at its lower end is filled with the contents and is converted to separate, closed packages. The contents are introduced via a delivery tube 2, which extends substantially horizontally into the tube above the growth end of the same and thereafter vertically downwards through the tube 1 and substantially co-axially with it to the region for the conversion of the tube to separate packages. The delivery tube 2 is surrounded co-axially by a further tube 3, which ends at and delivers air to a region somewhat above the outlet of the delivery tube 2. This air feed tube 3 carries at some distance above the outlet a helical source of ultra-violet rays 4, which is wound around the co-axial tubes 2, 3. The air feed tube 3, which at the same time serves as a reflector for ultra-violet radiation, has at its outlet a flange 5 to prevent ultra-violet irradiation of the contents present in the bottom end of tube 1. Below the outlet of the tube 3 is a screen 6, which is adapted to reverse the direction of the air flowing from the tube 3. Finally, a flange 7 is present at the bottom end of the filling tube 2, which prevents the contents during operation from splashing upwards against the sterilization arrangement.

This known filling and sterilization arrangement is complemented for the realization of the sterilization method in accordance with the invention with a further air delivery tube 8 which surrounds co-axially the upper part of the first-mentioned air delivery tube 3 and has a circular outlet directed downwards and situated above the upper end of the source of ultra-violet rays 4. The tube 8 extends like the tube 3 sideways out of the tube in the open longitudinal joint at the growth end of the tube 1. The tube 8 is connected via a valve device 9 to the tube 3 and constitutes thus a branching of the latter.

The arrangement in accordance with the invention comprises furthermore a tube 10, the one end of which is connected via a valve 12 to the delivery tube 2 for the contents. The other end of the tube 10 is connected via a valve 14 to a further tube 11, a fan 15 and a filter 16 which is connected via the valve 9 mentioned earlier to the tubes 3 and 8. The valve 14 also makes it possible to connect the tube 11 directly to the surrounding atmosphere. Finally, a valve 13 is present in the tube 2 to shut off the delivery of the contents, which valve is situated upstream of the junction point with the tube 10.

The arrangement in accordance with the invention operates as follows: when the machine is to be started, the valve 13 is closed, so that the contents are prevented from flowing to that part of the tube 2 which is situated downstream of the valve 13. The valve 14 is set so that the connection of the tube 11 with the outside atmosphere is closed and the connection between the tube 10 and the tube 11 is open. The valve 9 finally is set so, that the tube 11 communicates with the tube 8 as well as with the tube 3. As a result a duct is produced in which a circulation can take place. The duct comprises the delivery tube 2, the valve 12, the tube 10, the valve 14, the tube 11, the fan 15, the filter 16, the valve 9, the air tubes 8 and 3, together with the tube 1. The air present in this duct is made to circulate with the help of the fan 15, whereupon the source of ultra-violet rays 4 is activated. When the circulating air passes the source of ultra-violet rays 4 the oxygen present in the air is converted to ozone, which together with the air is extracted from the tube 1 through the delivery tube 2 and via the tubes 10 and 11 with appertaining units back into the tube 1 through the two air delivery tubes 8 and 3. The part of the ozone-air mixture which flows through the tube 8 then passes once more the source of ultra-violet rays 4, as a result of which a further part of the oxygen present in the air is converted to ozone. The more and more concentrated ozone mixture circulating sterilizes during the circulation the inside of that part of the packing material tube 1 which extends from the outlet of the air delivery tube 8 and downwards, the flanges 5, 6, 7, the outside surface of those parts of the tubes 3 and 2 which are located in the packing material tube 1, the inside of the tube 3, the inside of that part of the tube 2 which extends between the outlet in the packing material tube 1 and the valve 13, the tubes 10 and 11 with the valves 9, 12, 14 and the fan 15 together with the filter 16. The path of circulation of the ozone mixture is indicated on the drawing by broken-line arrows.

When the source of ultra-violet rays has been activated for a certain time, a sufficient amount of ozone has been formed to allow sterilization with the source of ultra-violet rays disconnected. Thus the source of ultra-violet rays need not be activated during the whole sterilization period but can, for example, be activated intermittently.

When the pre-sterilization has been in progress for the desired period and consequently is to be shut down, the valve 12 is closed. Furthermore, the valve 14 is changed over so that the tube 11 instead of communicating with the tube 10 is connected to the atmosphere. Finally, by means of the valve 9 the connection between the tube 11 and the air delivery tube 8 is interrupted, with the result that the fan 15 will suck air into the tube 11 via the valve 14 and blow the air out into the tube 1 via the filter 16 and the tube 3, whereupon the air, in known manner, is allowed to flow past the source of ultra-violet radiation 4 and out through the growth end of the material tube 1. This path of flow is indicated in the drawing by means of full-line arrows. Subsequently, the movement of the tube 1 commences and the valve 13 is opened so as to allow delivery of the contents to the bottom end of the tube, whereafter the manufacture of the separate packages is started. The filter 16 is a deep filter with a filling material, e.g. glass-wool, which filter is able to withstand the oxidizing effect of the ozone.

As can be seen from the drawing the circulation duct for the ozone mixture is not closed, since the material tube 1 is open towards the top. This is of no importance, however, since ozone is heavier than air and thus remains in the tube and prevents a mixing in of outside air. However, if it were necessary it would be quite possible of course during the pre-sterilization to close in a suitable manner the connection of the material tube to the outside air.

With the help of the method and arrangement in accordance with the invention a pre-sterilization system is provided which, among other things, thanks to the utilization of the source of ultra-violet rays already present, offers economically as well as technically substantial advantages.

It can readily be seen that the specific method and apparatus of the invention has been described and it is contemplated that changes may be made without departing from the scope or spirit of the invention and it is desired that the invention be limited only by the claims.

That which is claimed is:

1. A method to pre-sterilize a packaging machine which supplies a product through a filling tube into a web of paper and forms the web of paper into a succession of product filled packages comprising the steps of: providing a supply of air into the machine, converting a portion of the oxygen in the air to ozone by subjecting the air to radiation and recirculating the ozone produced through the filling tube of the machine for predetermined length of time.

2. The method of claim 1 wherein the radiation is in the form of ultra-violet rays.

3. Apparatus to produce a plurality of filled packages from a web of packaging material comprising: a product delivery tube, a supply of product connected in fluid-flow communication with said product delivery tube, a source of ultra-violet rays operably associated with said delivery tube, means to supply air past said ultra-violet ray source to convert a portion of the oxygen in the air to ozone, a duct system connected to said delivery tube at one of its ends and said means to supply air connected at the other of its ends to said delivery tube and means connected to said delivery tube to cut off the supply of product into said delivery tube and means to recirculate the ozone from said other end of said delivery tube through said tube and said duct system.

4. The apparatus of claim 3 wherein said duct system includes means to selectively open said duct to the atmosphere.

5. The apparatus of claim 3 wherein said duct system includes a filter having a filling material resistant to the action of ozone.

* * * * *

UNITED STATES PATENT OFFICE
CERTIFICATE OF CORRECTION

Patent No. 3,970,426     Dated July 20, 1976

Inventor(s) Sven Olof Soren Stark et al.

It is certified that error appears in the above-identified patent and that said Letters Patent are hereby corrected as shown below:

Assignee should read:

-- AB Ziristor, Lund, Sweden -- .

Signed and Sealed this

Thirtieth Day of November 1976

[SEAL]

Attest:

RUTH C. MASON
*Attesting Officer*

C. MARSHALL DANN
*Commissioner of Patents and Trademarks*